US009990827B2

(12) United States Patent
Vaddepally et al.

(10) Patent No.: US 9,990,827 B2
(45) Date of Patent: Jun. 5, 2018

(54) WIRELESS PATIENT CARE SYSTEM AND METHOD

(71) Applicant: RISTCALL LLC, Philadelphia, PA (US)

(72) Inventors: Srinath Vaddepally, Pittsburgh, PA (US); Ameya Bhat, Pittsburgh, PA (US); Yicheng Bai, Pittsburgh, PA (US)

(73) Assignee: RISTCALL LLC, Philadelphia, PA (US)

( * ) Notice: Subject to any disclaimer, the term of this patent is extended or adjusted under 35 U.S.C. 154(b) by 0 days. days.

(21) Appl. No.: 15/127,244

(22) PCT Filed: Mar. 18, 2015

(86) PCT No.: PCT/US2015/021331
§ 371 (c)(1),
(2) Date: Sep. 19, 2016

(87) PCT Pub. No.: WO2015/148225
PCT Pub. Date: Oct. 1, 2015

(65) Prior Publication Data
US 2017/0186301 A1    Jun. 29, 2017

Related U.S. Application Data

(60) Provisional application No. 61/954,874, filed on Mar. 18, 2014.

(51) Int. Cl.
*G08B 1/08*    (2006.01)
*G08B 21/04*    (2006.01)
(Continued)

(52) U.S. Cl.
CPC ..... *G08B 21/0446* (2013.01); *G06F 19/3418* (2013.01); *G08B 21/245* (2013.01);
(Continued)

(58) Field of Classification Search
CPC .......................... G08B 21/0446; G06F 19/322
(Continued)

(56) References Cited

U.S. PATENT DOCUMENTS 8,279,716 B1    10/2012 Gossweiler, III et al.
8,725,842 B1    5/2014 Al-Nasser
(Continued)

FOREIGN PATENT DOCUMENTS

EP    2784709 A2    1/2014

OTHER PUBLICATIONS

International Search Report dated Jan. 12, 2016 for corresponding PCT/US2015/021331.
(Continued)

*Primary Examiner* — Eric M Blount
(74) *Attorney, Agent, or Firm* — Michael D. Lazzara, Esq.; Leech Tishman Fuscaldo & Lampl

(57) ABSTRACT

A patient care system and a corresponding method that provide patient monitoring. The system includes a server, at least one patient communication device, and at least one caregiver communication device. The communication devices send receiving signals and notifications wirelessly to/from the server, and may be adapted to be worn on a user's wrist. Notifications can be sent to the caregiver communication device to notify the user to provide care to a patient in response to a patient request for assistance based on defined conditions, which may be proximity based. The server may track all received and sent notifications and may provide analytics of this information to improve quality of healthcare in a facility.

11 Claims, 9 Drawing Sheets

(51) Int. Cl.
*H04W 4/02* (2018.01)
*H04W 4/22* (2009.01)
*H04L 29/08* (2006.01)
*G06F 19/00* (2018.01)
*G08B 21/24* (2006.01)
*G08B 25/01* (2006.01)
*H04W 4/00* (2018.01)
*H04L 29/06* (2006.01)
*H04W 84/12* (2009.01)

(52) U.S. Cl.
CPC ........... *G08B 25/016* (2013.01); *G16H 10/60* (2018.01); *G16H 40/20* (2018.01); *H04L 67/12* (2013.01); *H04W 4/008* (2013.01); *H04W 4/023* (2013.01); *H04W 4/22* (2013.01); *H04L 67/42* (2013.01); *H04W 84/12* (2013.01)

(58) Field of Classification Search
USPC .................................................... 340/539.11
See application file for complete search history.

(56) References Cited

U.S. PATENT DOCUMENTS

| | | |
|---|---|---|
| 2005/0148890 A1 | 7/2005 | Hastings |
| 2006/0202816 A1* | 9/2006 | Crump ............... A61B 5/02055 340/539.12 |
| 2009/0091458 A1 | 4/2009 | Deutsch |
| 2010/0117836 A1 | 5/2010 | Seyed |
| 2012/0112903 A1 | 5/2012 | Kaib et al. |
| 2012/0313776 A1* | 12/2012 | Utter, II ............... A61B 5/0205 340/539.12 |
| 2013/0045685 A1* | 2/2013 | Kiani .................. G06F 19/3406 455/41.2 |
| 2014/0070939 A1 | 3/2014 | Halverson et al. |

OTHER PUBLICATIONS

Supplementary European Search Report dated Sep. 20, 2017 for EP 15770176.

\* cited by examiner

WIRELESS PATIENT CARE SYSTEM AND METHOD

CROSS-REFERENCE TO RELATED APPLICATION

This patent application claims priority to U.S. Provisional Patent Application No. 61/954,874, filed Mar. 18, 2014, and entitled "Wireless Wristband and Patient Care Platform," the content of which is incorporated herein by reference in its entirety.

BACKGROUND OF THE INVENTION

Technical Field

This invention pertains generally to a wireless communication system and software applications for use in a healthcare patient care setting. More specifically, the invention pertains to a platform for using wearable devices to provide patient care.

Description of the Related Art

Healthcare facilities rely on nurses and nurse assistants to provide timely and compassionate care. Current facilities use call buttons which, when depressed by a patient in need of assistance, send a signal to a central nursing station. Existing call button systems pose several problems for the patient and nurse alike. Most critically, they are tethered to the bed or to the wall near the bed, and thus can result in the call button being out of reach if the patient is not in bed when they need help. Further, the signal is sent to a central nursing station which may not be currently staffed (e.g. all the nurses may be occupied with other patients), or may be staffed by an administrator who registers the call but does not directly respond to the call. That is, the administrator may route the call to a nurse or may turn on a call light outside the patient's room. In both scenarios, there is no information regarding whether a nurse has been allocated to the call or is available to respond to the call, and there is no tracking of when the call was answered or even if the call was answered. All of this increases the response time, effects the patient experience, and delays patient care.

Additionally, the current call button system has no way to track call response times or provide dynamic feedback regarding response times. Further, such systems do not provide administrators with information on patient acuity, which is the categorization of a patient according to an assessment of their nursing care requirements. Staffing issues have long been of concern at most health care facilities, and can influence the safety of both the patient and the nurse. There is a strong relationship between adequate nurse-to-patient ratios and improved patient outcomes. Rising patient acuity and shortened hospital stays have contributed to these challenges. Additionally, current call button systems do not allow anonymous patient driven feedback on the kind of care they received for the type of request raised.

Wearable smart devices, such as smart watches, have been a source of much recent innovation. For example, U.S. Pat. No. 8,279,716 shows a smart-watch including a processor, a wireless transceiver for use with Wi-Fi, and a tactile user interface. The content of this patent is hereby incorporated by reference in its entirety. Furthermore, where a definition or use of a term in a reference, which is incorporated by reference herein is inconsistent or contrary to the definition of that term provided herein, the definition of that term provided herein applies and the definition of that term in the reference does not apply.

Such a wearable device in the care setting would allow a patient or caregiver to communicate from any location, a much needed ability. However, applications of such wearable devices in the field of healthcare are still lacking, and existing applications have not taken advantage of their capabilities. While the use of smart devices in healthcare services has been explored, they are still lacking in many of the same areas that traditional call bells are lacking. For example, European Patent Application EP 2784709 considers the use of a smart device, such as smart phone or tablet, to control many of the electronic devices in a hospital room, but ties such a device to an older nurse call system. Such devices also do not solve many of the problems existing in traditional nurse call systems. For example, there is no visible indication of accountability to others. Communications are paired; that is, one patient is paired with one caregiver.

Therefore, there is a need for a system that does not pair one patient with a single caregiver, but rather can allow any on-duty caregiver to attend to the patient, and without having to rely on a centralized nursing station. Also, there is a need for a system that can deliver a notification based on a condition, such as a patient fall, or to prevent a patient from being lost.

SUMMARY OF THE INVENTION

The present invention addresses the above-mentioned and other needs in the art by providing patient care systems and methods for use in a healthcare facility that enable more responsive and accountable patient care.

In an exemplary embodiment, the system includes a server with means for sending and receiving wireless communications. The system may further include a patient communication device and a caregiver communication device that wirelessly communicate with the server. The patient communication device, which may be adapted to be worn on the patient's body, may include a user interface, and a wireless communication means for sending an assistance signal to the server. The caregiver communication device, which also may be wearable, may include a user interface, a wireless communication means for receiving a notification signal from the server, and a display which indicates that notification signal. The server may include a server memory, which stores server instructions and a server processor for executing these instructions. When the instructions are executed, the server processor may send a notification signal to a combination of the caregiver or patient communication devices. This may be dependent upon certain preset conditions being satisfied, or upon the receipt of an assistance signal. The server may also be configured to track each of these signals. The patient and caregiver communication devices also each include a processor and a memory which stores instructions for execution by the processor to implement the device's functions, and to provide the indications on displays described herein.

The patient and caregiver communication devices may include a client memory storing client instructions and a client processor which executes these client instructions. It is possible that these instructions are the same for both communication devices, though they can be operable in different modes for the different types of communication devices. These communication devices may be adapted to be wearable on a patient or caregivers, for example on the wrist, waist, or neck.

The patient or caregiver communication devices may further include a proximity detector. Their respective wireless communication means may then send an arrival signal to the server when the two devices come into a certain proximity to each other, and the server may then track these arrival signals. The wireless communication devices may also exchange communications directly between the devices.

The patient communication device may include a call button, which may send a notification signal to the server. The server may then send a notification signal to a chosen combination of the caregiver communication devices. The patient communication device may also include classification buttons, as well as indications as to how many times they have requested service, and how long their request has been open. Its user interface may also include feedback buttons to send a feedback signal to the server, and the server may then track these feedback signals. The feedback buttons may be configured such that they may be available to the patient once the caregiver has exited a certain proximity to the patient.

The caregiver communication device may also have a display. This display may show each notification it has received. If the caregiver communication device receives multiples of the same request, this acuity data may be indicated on the display. This may be in the form of a count of the number of times the caregiver communication device has received a notification signal from that source. This notification signal may also include a patient identification, patient's location, the time of the call, and the nature of the patient's request.

The patient care system may also include devices and software for wander detection. For this, the system may include wander beacons. Once again, the patient communication devices may use a proximity detector. The patient communication device's wireless communication means may send a wander signal to the server when its proximity detector detects that the wander beacon is in its proximity. The server may receive this wander signal and send a wander notification to a combination of caregiver communication devices.

The patient care system may also include devices and software for hand hygiene detection. For this, the system may include hand hygiene beacons. The caregiver communication device may use a proximity detector and an accelerometer. The wireless communication means of the caregiver communication device may then be configured to send a hand hygiene signal to the server. The server may receive this signal and be configured to calculate a time duration based on the hand hygiene signal, which is an amount of time the caregiver was sanitizing her hands. The server may then determine whether a hand hygiene notification to the caregiver communication device. This may be because the time the caregiver spent sanitizing her hands did not satisfy a preset time condition. It may also be because the caregiver communication device did not satisfy certain proximity conditions, such as being near to a hand hygiene beacon, or triggering its touch sensor.

The system may also make use of a call light device. This call light device may include a wireless communication means for receiving a status signal from the patient communication device. It may also have an indicated light which can change colors, which may indicate the status of a patient call. The wireless communication means of a patient or caregiver communication device may be configured to send status updates to the call light to device, communicating these status changes.

Both the patient and caregiver communication devices may also provide on-demand location to an administrator. This may again involve the use of included proximity detectors. Their wireless communication means may be configured to send a patient or caregiver location to the server. This location may include a both a macro-location and a micro-location. The micro-location may be based on the communication device's proximity to other communication devices, call light devices, and other beacons. The server may be configured to receive this information, and send a patient or caregiver location notification to any combination of caregiver communication devices.

The server may also display a dashboard. This dashboard may depict care analytics and adjustable parameters for sending notification signals. The server may also receive battery status data from both patient communication devices and caregiver communication devices, and then display this information on the dashboard. The dashboard may display analytics based on the information received from the patient or caregiver communication devices. This may include: a response time monitor, a monitor showing all open requests, a monitor showing the time spent at patients' bedsides, a nurse location monitor, a rounding alert monitor, a fall detection monitor, a patient satisfaction score monitor, a monitor tracking the location of each device, a monitor showing the activity level of each device, a monitor for tracking bed exit alarms, a noise level monitor, a monitor showing the caregivers' forwarded calls or requests for help, a monitor of caregivers' communications with other caregivers or departments, a monitor of all voice communications, a patient wander detection monitor, a hand hygiene monitor, a patient vital sign collection monitor, and monitors showing patient and caregiver profiles. The server may also integrate this information with admission, discharge, and transfer (ADT) record and Electronic Medical Record (EMR) for digital transfer of the patient profile information to and from the EMR and ADT records.

The caregiver communication devices' displays may also display a list of each open notification which has been received by that caregiver communication device. The server may be configured to send a completion signal to the caregiver communication device when preset conditions have been satisfied. Upon receiving this completion signal, the caregiver communication device may no longer indicate the notification signal.

The caregiver communication device may also use its wireless communication means to request assistance from another caregiver. The wireless communication means may be configured to send an assistance signal to the server. The assistance signal may include asking for additional help or forwarding the call to other caregivers. The server may receive this assistance signal and then send a help notification to other caregiver communication devices, which may indicate that another caregiver requires assistance.

The caregiver may also set a reminder on the system. The caregiver communication device's wireless communication means may send a reminder signal to the server. Then, the server may receive this signal, wait a period of time, and then send a reminder notification to a caregiver communication device. Preset conditions may also be set on the server for automatic rounding reminders. These automatic rounding reminders may send notification signals to caregiver communication devices at preset intervals to visit inactive patients. This may be determined by nursing administrators or server analytics based on patients' activity levels.

The system may also facilitate voice communication. For this, the patient communication may include a microphone, and its wireless communication means may be configured to send a noise level signal to the server based on data recorded by the microphone.

In another embodiment, the system may include a patient microphone and a patient speaker. A patient communication device's wireless communication means may then be configured to send a voice signal to the server. Similarly, the caregiver communication device may include a microphone and a speaker and use its wireless communication means to send a voice signal to the server. The server may then send a voice message to any of the caregiver or patient communication devices. The patient communication device and nurse communication device may alternatively communicate with each other through voice in real time.

The patient communication device may also include an accelerometer, and its wireless communication means may, based on this, send a movement level signal to the server. Based on this data, the server may then send a fall notification to a caregiver communication device based on a particular movement level signal. Alternatively, based on this data, the server may send a patient adjustment notification to a caregiver communication device based on a particular movement level signal. This may indicate that the patient has been in one position for too much time, and is at risk of developing bed ulcers, or may have fallen. The caregiver communication device may also include an accelerometer. Then, either a caregiver communication device or a patient communication device may send activity level data to the server.

BRIEF DESCRIPTION OF THE DRAWINGS

The detailed description will refer to the following drawings in which like numbers refer to like items, and in which.

DETAILED DESCRIPTION OF THE INVENTION

Figure 1:
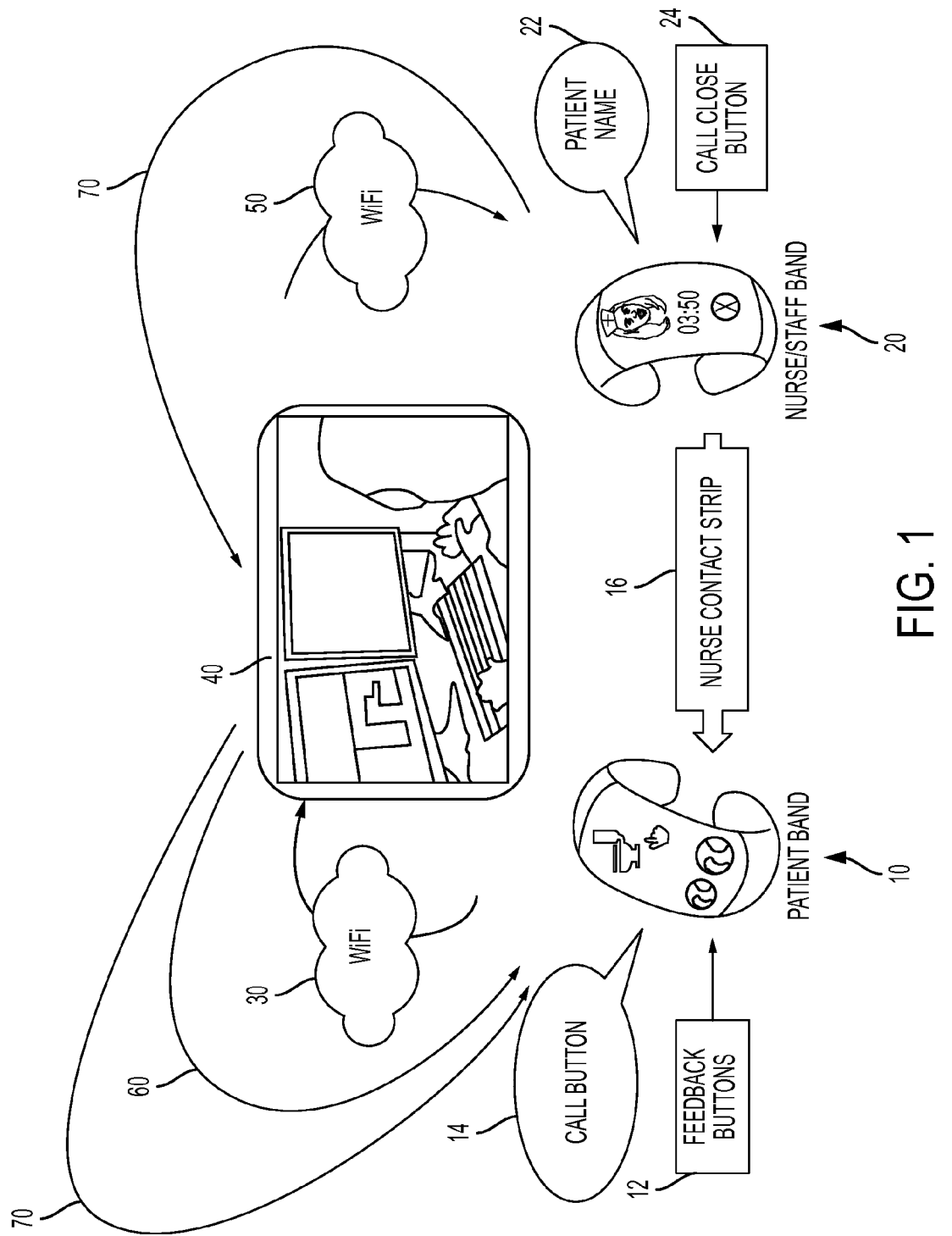
FIG. 1 illustrates an embodiment of a patient care system of the invention where the patient and caregiver have wristband communication devices.

FIG. 1 is illustrative of an embodiment of a patient care system of the invention where the patient and caregiver have wristband communication devices that enable communications, such as the communications required for a patient to call a caregiver for care. In this embodiment, the patient and caregiver communication devices have been described as wristbands. A caregiver may be a nurse, family member, or any other person who provides care to another. In alternate embodiments, the patient and caregiver communication devices may be any of a wristband, a fob or pendant which may be connected at the waist or around the neck, a smartphone, or any device which may be adapted to be worn and may be easily accessed. Alternatively, the patient and caregiver communication device may be any device that can be easily carried.

When a patient wishes to be attended to by a caregiver, the patient may actuate a call button 14 on their patient communication device 10. This will cause the patient communication device 10 to transmit an assistance signal 30 to a server 40. The assistance signal may be sent over Wi-Fi, or any other wireless network that would facilitate transmission of a wireless signal. This may for example be done using a standard internet protocol or a local area network. The server 40 will then send a notification signal 50 to a caregiver communication device 20, again on the same network. The server 40 may also send an acknowledgment signal 60 back to the patient communication device 10. The patient communication device 10 may then indicate this acceptance signal to the patient. Exemplary means for wireless communication used by the patient communication device 10, caregiver communication device 20, and the server 40 are well known in the field of wireless communications, and include any circuitry which may transmit or receive a wireless signal. The notification signal 50 may be displayed on the caregiver communication device 20, which may include displaying the patient's name 22 or other information.

In an embodiment, the caregiver may interact with the notification signal 50 to send an acceptance signal 70 to the server 40. The server 40 may then send an acceptance signal 70 to the patient communication device 10. The patient communication device 10 may indicate that a caregiver has accepted a request or notification, or that a caregiver is en route to the patient's location.

Upon seeing the notification signal displayed on their caregiver communication device 20, a caregiver may attend to the patient in his room. In an embodiment, the patient and caregiver communication devices may further include a nurse contact strip 16. That is, the nurse contract strip 16 of the caregiver communication device 20 may be touched, or come into nearby proximity, to the nurse contact strip 16 on the patient communication device 10 to register a care interaction. In a manner analogous to satisfying a conventional call from a call button, the caregiver may press a call close button 24 when the service has been provided. In this manner, the call close button is under the caregiver's control, which may allow the caregiver to keep a call open even after the caregiver's proximity to the patient may have indicated that the patient contact or interaction has occurred. After the caregiver has satisfied the reason for the patient's call, the patient may have opportunity to provide feedback on feedback buttons 12.

The patient and caregiver communication devices each have a memory which stores programmed code, and a processor to implement that code. In an embodiment, the patient and caregiver communication devices may be the same physical device, and have the same code installed on their memory. Thus, when executed, a communication device would be capable of being operated as either a patient or caregiver communication device. In this embodiment, a user may be presented with an initial election between operating the communication device in a patient mode or in a caregiver mode.

In an embodiment of the system, the patient communication device 10 will begin in a passive state waiting to receive an input. Once the patient communication device 10 receives an input, for example a patient pressing the call button 14, the patient communication device 10 will be programmed to send an assistance signal 30 to the server 40. When the patient communication device 10 receives an acknowledgment signal 60 in response, it may then be programmed to indicate to the patient that a call has been sent. The patient communication device 10 then remains in a passive state until either a caregiver arrives to provide the requested care, or the patient communication device 10 receives an acceptance signal. If the patient communication device 10 receives an acceptance signal from the server 40, it may be programmed to indicate to the patient that a caregiver has accepted the assistance request, or that a caregiver is en route. The patient communication device 10 may be programmed to recognize a caregiver within proximity, or a caregiver communication device 20 contacting its nurse contact strip 16. The patient communication device 10 may then be programmed to register this as meaning that a caregiver has arrived at the patient's location. The caregiver may then actuate call close button 24, indicating that the caregiver has completed providing care to the patient. The patient communication device 10 may then be programmed to prompt the patient for feedback and process this feedback received from a user input.

Likewise, the caregiver communication device 20 will begin in a passive state waiting to receive an input. Once the caregiver communication device 20 receives an input, for example notification signal 50, the caregiver communication device 20 may be programmed to indicate this to the caregiver by indicating on its display the patient's name and related information. In an embodiment, the caregiver communication device 20 may then be programmed to accept an input from the caregiver that would indicate that the caregiver has accepted the call. The caregiver communication device 20 may then transmit an acceptance signal 70 to the server 40. The caregiver communication device 20 will then remain in a passive state until receiving an input indicating that the caregiver is in proximity of the patient. This may be an input via a contact of the nurse contact strip 16, or other proximity detection. After the caregiver has provided care to the patient, the caregiver communication device 20 will return to its initial passive state, waiting to receive another input. In an alternative embodiment, the caregiver communication device 20 may be programmed to remain in the passive occupied state keeping the call open until the caregiver presses call close button 24, at which point the caregiver communication device 20 would return to its initial passive state.

Finally, server 40 will remain in a passive state until its programmed code recognizes a condition indicating it should send a signal. In an embodiment, this may be a certain input, such as an assistance signal 30. In an alternative embodiment, this condition may be the server 40 recognizing that a certain patient communication device 10 has not raised a call for a set amount of time, and thus the patient needs to be checked on. The server 40 may then be programmed to automatically send an acknowledgment signal 70 to the patient communication device 10, and a notification signal 50 to a caregiver communication device 20. The server 40 may also be programmed such that when it receives an acceptance signal 70 from a caregiver communication device 20, it will then transmit a corresponding acceptance signal 70 to the patient communication device 10 whose request was accepted. The server 40 may also be programmed to track the receipt and transmission of each signal for further use and analysis, which may be made available to a server administrator.

Other embodiments exist which may also trigger the server 40 to send a substantially similar notification signal to a caregiver communication device 20. For example, a caregiver may set an automatic reminder for himself, where the server 40 will send the caregiver a notification signal after a set amount of time has passed. An administrator, or programmed code on the server 40, also may set automatic rounding alerts using software at server 40, which would send a notification signal to any specified caregiver communication devices 20 at specified intervals if, for example, a patient needed to be checked on every certain number of hours.

Many features of the system of the invention rely on proximity detection. There are several methods for proximity detection known by those of ordinary skill in the art. Any of these methods for proximity detection would work within the scope of this invention. For example, Bluetooth, or Bluetooth low energy (BLE) may be used. Alternatively, radio-frequency identification (RFID), near field communication (NFC), or infrared (IR) would all be similarly effective for these purposes.

Figure 2:
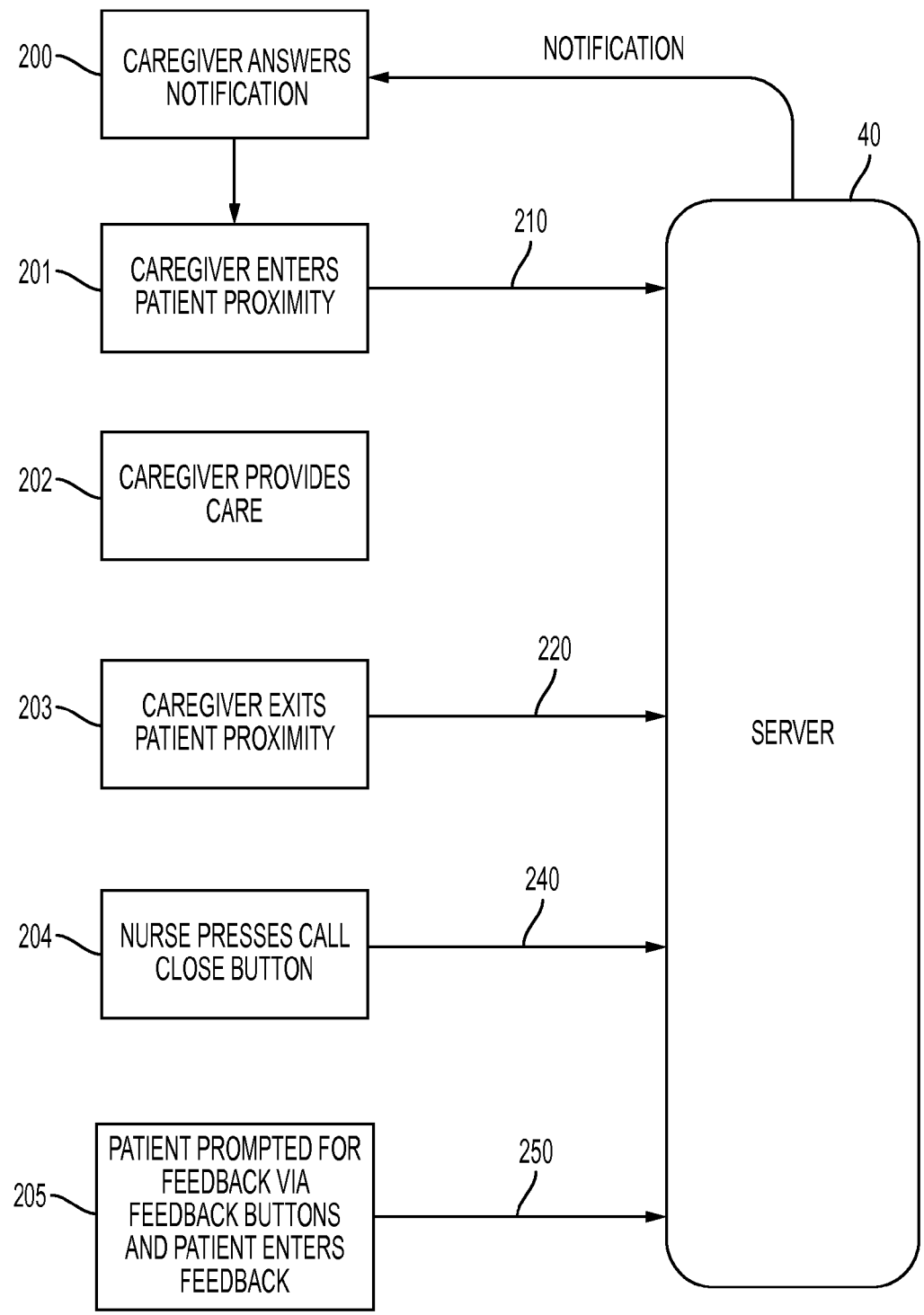
FIG. 2 is a flowchart illustrating one embodiment of the process of a caregiver's response to a patient and the patient's subsequent feedback.

FIG. 2 shows more in-depth one possible embodiment of a process by which the caregiver provides care to a patient and the patient provides feedback on this care. This process involves the use of proximity detection on the caregiver and/or patient communication devices. The process begins with block 200, when the caregiver answers the notification from the server 40. The caregiver may make an indication of this on their caregiver communication device 20, or may simply enter the patient's room or immediate vicinity, as in block 201. Upon entering the patient's proximity, either the patient communication device 10 or the caregiver communication device 20 may transmit an arrival signal 210 to the server 40, which the server 40 may track. Next, at block 202, the caregiver will provide the requested care. After providing the requested care, the caregiver will exit the patient's proximity, as in block 203. Upon leaving the patient's proximity, either the patient communication device 10 or the caregiver communication device 20 may send a departure signal 220 to the server 40. Again, the server 40 may track this signal. The server 40 keeps track of all signals and patient acuity levels, caregiver response times, caregivers' time spent at patients' bedsides, patient feedback data, and other data based on the signals. That is, the patient acuity may be classified based on call number and call type as identified by the caregiver. Such data may allow healthcare administrators to more accurately and dynamically manage personnel resources, costs, and quality.

After the caregiver has provided care to the patient, in box 204, the caregiver may press a call close button 24 on the caregiver communication device 20. This may be done at the patient's bedside, or after leaving the patient's bedside. This may transmit a call close signal 240 to the server 40, which will signal to the server 40 that the call has been completed. The patient would be prompted for feedback on their patient communication device 10 via feedback buttons 12 at 205. This may be in the form of a "thumbs up" or "thumbs down" election. A "thumbs up" button may allow the patient to indicate if the caregiver's response was positive or if the encounter was a good encounter. A "thumbs down" button may allow the patient to indicate if the caregiver's response was negative or if the encounter was a poor encounter. These buttons may be labeled by in other similar manners, such as: pictures (for example, thumbs up or thumbs down), words (for example, good or bad), colors (for example, red or green), or emoticons (for example, a happy face or an unhappy face). When this selection is made, the patient communication device 10 will send a feedback signal 230 to the server 40, which again may be logged by the server 40. In an embodiment, the feedback buttons 12 may only become available after the caregiver has actuated the call close button 24 on the caregiver communication device 20. The feedback buttons 12 may also only be activated when the caregiver communication device 20 is outside of a range of the patient communication device 10.

This range may be defined based on the environment of the patient care setting. For example, in a setting having private patient rooms, the range may be set to a distance that would indicate the caregiver has left the patient's rooms. Alternatively, in a facility where the patient may be in a closer proximity to other patients who may require care, the range may be lowered to adjust for the possibility that the caregiver may remain in the same vicinity caring for other patients. In all cases, the range may be set so that only the patient would be able to provide the feedback. Additionally, such ratings may be made anonymous by masking the identity of the patient and/or the caregiver. In this way, rating feedback may be provided based on a hospital unit, division, or floor and not for specific patients and/or caregivers. This data can be aggregated and analyzed by the server 40. If a patient regularly presses the thumbs down button for a bad encounter, the server 40 may have code which provides a statistical tool to determine if the patient always gives a bad evaluation. This data may be utilized by a system administrator to improve the facility's Hospital Consumer Assessment of Healthcare Providers and Systems (HCAHPS) score.

In this embodiment, the patient communication device 10 may be programmed such that it is in a passive state after receiving an acceptance signal 70. Once a caregiver communication device 20 enters the proximity of the patient communication device 10, the patient communication device 10 may be programmed to send an arrival signal 210 to server 40. The patient communication device 10 may then remain in a passive state until the caregiver communication device 20 exits its proximity at which point the patient communication device 10 may be programmed to transmit departure signal 220 to the server 40. Then, if the caregiver communication device 20 is no longer in proximity, and the caregiver communication device 20 has closed the call by actuating the close call button 24, the patient communication device 10 may be programmed to automatically prompt the patient for feedback. Then once the patient communication device 10 detects the input of the patient's feedback, it will transmit feedback signal 230 to the server 40. After this, as the caregiver interaction is complete, the patient communication device 10 will be programmed to go back into a passive state.

Alternatively, the caregiver communication device 20 may be programmed such that after accepting a notification and transmitting acceptance signal 70 back to the server 40, the caregiver communication device 20 will enter a passive state. Once the caregiver communication device 20 enters the proximity of that patient communication device 10, the caregiver communication device 20 may be programmed to send an arrival signal 210 to server 40. The caregiver communication device 20 may then remain in a passive state until it exits the proximity of the patient communication device 10, at which point the patient communication device 20 may be programmed to transmit departure signal 220 to the server 40. The caregiver communication device may also be programmed to transmit a call close signal 240 to the server 40 when the caregiver actuates a call close button 24 on the caregiver communication device 20. After this, the caregiver communication device 20 may be programmed to maintain a passive state until receiving a new input.

Finally, the server 40 may be programmed to remain in a passive state after receiving an acceptance signal 70 from a caregiver communication device 20 and thus transmitting an acceptance signal 70 to the patient communication device 10. The server 40 will be programmed to record an arrival signal 210, which it may receive from a caregiver or patient communication device. The server 40 will then later similarly record a departure signal 220 received from either a caregiver or patient communication device. The server 40 may continue to remain passive while accepting and recording a feedback signal 230 from the patient communication device 10. The server 40 may be independently communicating with any number of other communication devices during this process, just at it may outside of this process.

Server 40 may be located at a centralized desk in the facility, at a remote facility, in a "cloud" or any other conceivable location. The server 40 may also be accessible by a caregiver via a caregiver access point within the patient's room. Server 40 may also have software installed on it for generating and presenting a dashboard that, in turn, may depict care analytics and adjustable parameters for sending notification signals. The server 40 may be able to provide administrative data and statistics related to the number of calls placed, response times, service times, the most efficient nurses, the fastest nurses, call types and ratings to look for outliers (e.g. which floors of the facility are doing well and which are not). The server 40 keeps track of all signals and notifications that it receives and sends. In certain embodiments, the server instructions may include collecting information to provide analytics, for example advanced machine learning algorithms and analytics may be used to derive meaningful predictions and decisions based on the data collected from the patient and caregiver communications.

Examples of the analytics available on the dashboard may include statistics related to the number of calls placed, response times, service times, and call types and ratings to look for outliers. The response time may be based on proximity sensing of patient call time and nurse arrival time. It may track time spent at a patient's bed side by the time difference between the caregiver's arrival time and call closure time. It may also provide analysis of the received evaluations, and may adjust ratings for a particular patient's tendency to rate higher or lower. It may calculate the overall amount and proportion of a caregiver's time spent at bedsides through aggregating the time spent within proximity of a patient. It may further monitor all of the communication devices in the system for such data as their location, their connection status and their battery status.

Further, the server 40 may be configured through software applications to receive vital sign data and other sorts of health measurements from various digital collectors. It can aggregate this data and provide it in an Electronic Medical Record (EMR). For example, the server 40 may be compatible with digital devices that measure blood pressure, weight, blood sugar, pulse, height, respiration, temperature, and blood oxygen levels. The server 40 may further provide this information to the caregiver communication devices 20 to assist in the patient care. Additionally, the server 40 may aggregate admission, discharge, and transfer (ADT) data, which may be similarly accessible to the system's operators. The server 40 may also collect activity level data sent to it by the patient or caregiver communication devices 10. This data can be analyzed to provide a user with data relating a patient or caregiver's steps that day, as well as analyzing their time spent in various states. For example, an accelerometer on a patient communication device 10 may detect that a patient's activity level is very low, and by sending this data to the server 40, the server 40 can determine an amount of time the patient has spent sleeping. The accelerometer may also be used to detect the distance walked by the patient, how long the patient slept, and whether their sleep was light sleep or deep sleep. The server may also track this accelerometer information on the EMR.

Figure 3:
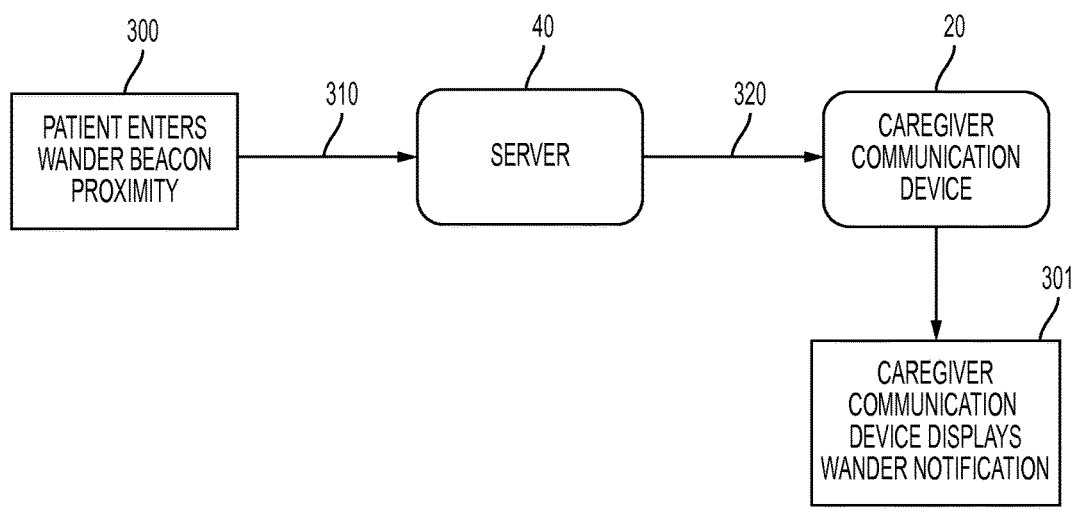
FIG. 3 is a flowchart illustrating a method of providing patient wander notifications to a caregiver.

Another possible use of the proximity capabilities of the patient's communication device 10 are in wander detection, a simple exemplary embodiment of which is represented in FIG. 3. In this embodiment, wander beacons may be placed around areas of the facility within which the hospital staff may want to restrict the patient. For example, a wander beacon may be placed outside a patient's door, at the exit of a hospital wing, at the front door of a nursing care facility, or at any location where the patient is not permitted to access. Beginning in block 300, a patient who is walking or otherwise moving around a hospital may come into proximity of a wander beacon, which would be detected by a proximity detector on the patient communication device 10. This may trigger the patient communication device 10 to send a wander signal 310 to the server 40. Which particular beacons would trigger a notification can be configurable by an administrator to each particular patient, as each patient may have different needs, which can all be accommodated.

The server 40 processes this wander signal 310, and then sends a wander notification 320 to any designated caregiver communication device 20. Which of the caregiver communication devices 20 this is sent to may be configured by an administrator based on, for example, proximity to the wander beacon that caused the patient communication device 10 to issue the wander signal 310. It may be a specific caregiver or group of caregivers assigned to that patient, or it may be every caregiver on the floor, or any other combination of caregivers. Finally, after receiving the wander notification 320, the caregiver communication device 20 may display the wander notification signal. Such a display may include the patient's name, room number, and/or other useful information. Once the notification is displayed on a caregiver communication device 20, the caregiver may proceed to locate the patient based on that information, allowing the caregiver to attend to the patient in a similar manner to a call raised by the patient himself.

In an embodiment, the patient communication device 10 may notify the server 40 each time it enters proximity to a beacon. For example, when the patient communication device 10 enters proximity to a hand hygiene beacon or call light device, the patient communication device 10 may send a notice to the server 40, which the server 40 may then record. Then, when the patient enters proximity to a wander beacon, the server 40 may display on its dashboard a history of all beacons the patient communication device 10 has been in proximity to before reaching the wander beacon. In this manner, an administrator accessing the server 40 will better be able to determine the patient's path to better facilitate locating the patient.

The patient communication device 10 may have code programmed such that the patient communication device 10 remains in a passive state until it detects that it is in proximity to a wander beacon. The patient communication device 10 may then be programmed to send a wander signal 310 to the server 40. The patient communication device 10 may then remain in a passive state until it detects a caregiver communication device 20 in its proximity or receives an acceptance signal, at which point it may proceed in a similar manner to a patient initiated call. The patient communication device 10 may also programmed to notify the server 40 each time it enters into proximity to a beacon (for example, a hand hygiene beacon or call light device.) The caregiver communication device 20 may be programmed to remain in a passive state until it receives a wander notification 320. Then, the caregiver communication device 20 may display a wander notification, which may then be accepted in a similar manner to a notification signal.

The server 40 may be programmed to maintain a passive state until it receives a wander signal 310 from a patient communication device 10. After receiving the wander signal 310, the server 40 may be programmed to send a wander notification 320 to a caregiver communication device 20. The server 40 will then enter into and remain in a passive state until receiving an acceptance signal or other signal as normal. The server 40 may be independently communicating with any other number of devices during this process. The server 40 may be programmed to receive a notice from a patient communication device 10 indicating that the patient communication device 10 entered into proximity to a beacon. The server 40 may then track all of these notices, and upon sending a wander notification 320 to a caregiver communication device 20 the server 40 may be programmed to display each of these notices from the patient communication device 10 on its dashboard.

Figures 4A, 4B, 4C:
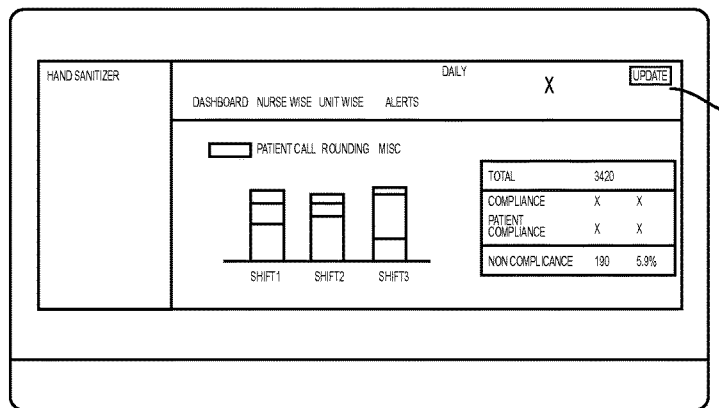
FIG. 4a illustrates a possible embodiment of the dashboard of the server showing wander alerts and patient locations.
FIG. 4b illustrates a possible embodiment of the dashboard of the server showing hand sanitizer analytics.
FIG. 4c illustrates a possible embodiment of the dashboard of the server showing a request monitor.

FIG. 4a illustrates a possible embodiment of the dashboard 410 of the server 40 showing wander alerts and patient locations. In this embodiment, the dashboard may display a list of wander alerts 401. This list of wander alerts 401 may indicate the location of the wander alert, time of the wander alert, how long has elapsed since the wander notification, and the current status of the wander alert, such as "alert sent." The dashboard 401 may also display patient locations 402. This may include further information, such as the battery level of their patient communication devices 10.

FIG. 4b illustrates a possible embodiment of the dashboard 410 of the server 40 showing hand sanitizer analytics. The analytics may show the percentage of caregiver interactions which were in compliance with hand hygiene policies. This embodiment also depicts a possible arrangement of links to other analytics screens.

FIG. 4c illustrates a possible embodiment of the dashboard 410 of the server 40 showing a request monitor. In this embodiment, the dashboard 410 may display every alert that the server 40 has sent to a caregiver communication device 20. The display may also show the classification of the request, the time of the request, elapsed time since the request, the location of the request, the acuity of the request, as well as any responses that have been carried out in regards to the request.

Figure 5:
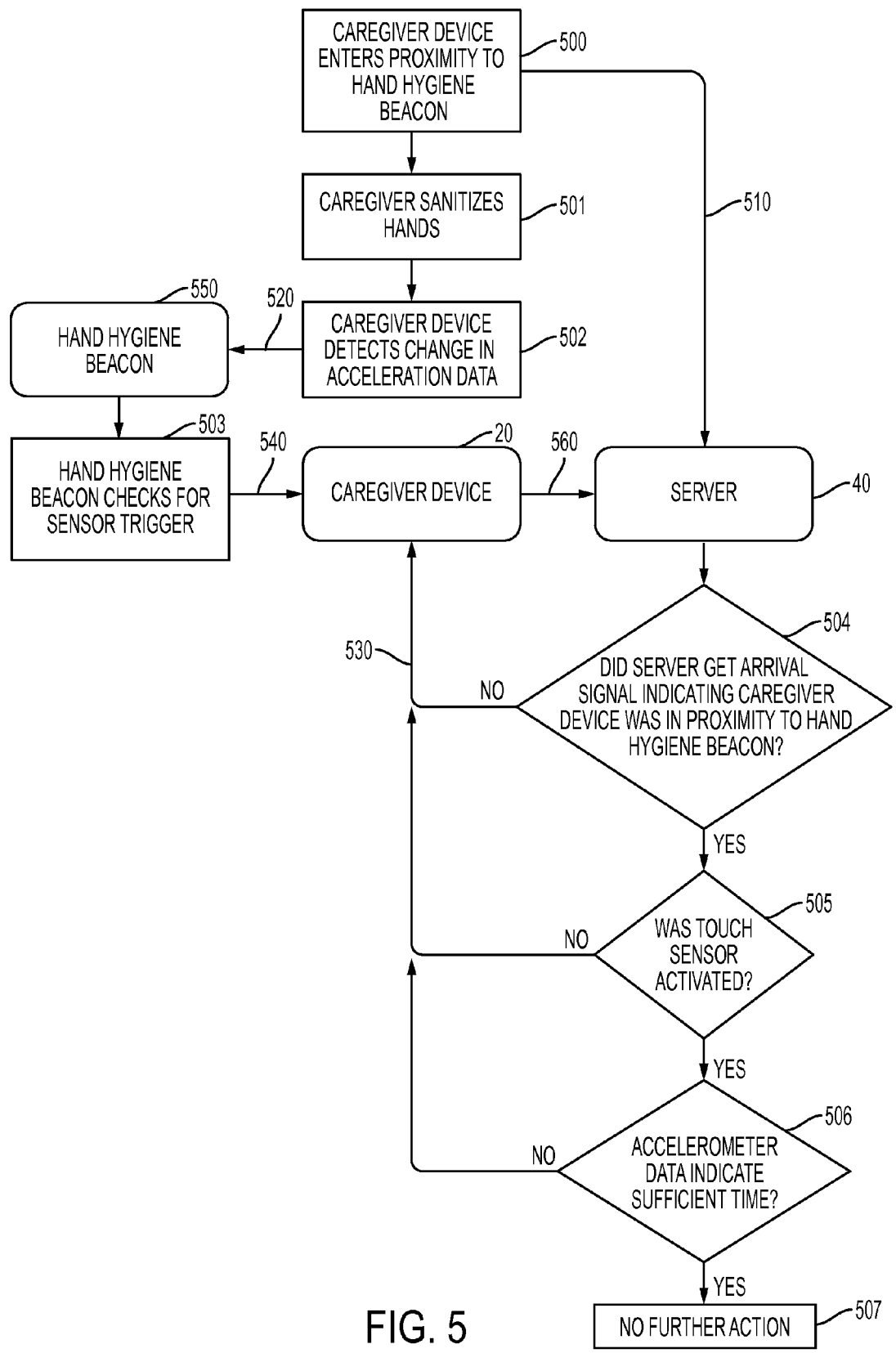
FIG. 5 is a flowchart illustrating the process of the system sending a hand hygiene notification to a caregiver.

FIG. 5 depicts an embodiment of a process of sending hand hygiene notifications using the system of the present invention. This embodiment provides one possible layout of devices used in the hand hygiene reminder process. In this example, a caregiver may be responding to a call, checking on the patient, or otherwise approaching the patient or his room. A hand hygiene beacon 550 may be located just outside of a patient's room. The hand hygiene beacon 550 may be placed near or directly on a hand sanitizing device, as typically used in hospitals. The hand hygiene beacon 550 may also be centralized in a wing or area of the facility, or at any other location, and the process would remain the same. The hand hygiene check process may be initiated by the caregiver entering proximity to the hand hygiene beacon. In an alternative embodiment, the hand hygiene check process may be initiated by entering proximity to the patient.

Beginning at block 500, a caregiver carrying a caregiver communication device 20 enters the proximity of a hand hygiene beacon 550. This will trigger the wireless communication means of the caregiver communication device 20 to send an arrival signal 510 to server 40. The server 40 will track this arrival signal 510 for a later determination in the process. Then, in block 501, the caregiver will spend an amount of time sanitizing her hands. This may then cause an accelerometer built into the caregiver communication device 20 to detect a change in acceleration at block 502. Once it is detected, the caregiver communication device 20 may then send this accelerometer data 520 to the hand hygiene beacon 550. When the hand hygiene beacon 550 receives the accelerometer data 520, in block 503 the hand hygiene beacon will then determine whether its touch sensor has been activated. This touch sensor may be activated by a physical touch, by capacitive-field-sensing technology, or any other technology for a switch mechanism which are well known by those of ordinary skill in the art.

The hand hygiene beacon 550 may then send this determination to the caregiver communication device 20 in the form of touch sensor data 540. After receiving the touch sensor data 540, the caregiver communication device 20 may combine it with the accelerometer data, and transmit all of this information to the server 40 as hand hygiene signal 560. The server 40 will then analyze this hand hygiene signal 560 to determine whether to send a hand hygiene notification 530 to the caregiver communication device 20. First, in block 504, the server will check whether the caregiver communication device 20 was within proximity to the hand hygiene beacon 550, indicated by whether the server 40 received an arrival signal 510 from the caregiver communication device 20. If the server 40 did not receive an arrival signal 510 indicating the caregiver communication device 20 was in proximity to a hand hygiene beacon, it will send a hand hygiene notification 530 to the caregiver communication device 20, indicating that the caregiver should wash her hands. If the server did receive the arrival signal 510, in block 505 the server 40 will then check whether the touch sensor was activated, based on the received hand hygiene signal 560. If the hand hygiene signal 560 indicates that the touch sensor was not activated, the server 40 will send a hand hygiene notification 530 to the caregiver communication device 20.

If the hand hygiene signal 560 indicates that the touch sensor was activated, then in block 506 the server will check whether the accelerometer data contained in the hand hygiene signal 560 indicates that the caregiver spent sufficient time sanitizing her hands. This may be determined according to a preset parameter for how long a caregiver must spend sanitizing her hands. If the server accelerometer data contained within the hand hygiene signal 560 indicates that sufficient time was spent, the inquiry will end in block 507, and no further action relating to the hand hygiene system will be taken. However, if the server 40 determines that sufficient time was not spent sanitizing, the server 40 will send a hand hygiene notification 530 to the caregiver communication device 20, reminding the caregiver to go back to a hand sanitizing station, thus contributing to overall facility cleanliness.

The caregiver communication device 20 may be programmed such that it is in a passive state until entering the proximity of a hand hygiene beacon 550. At this point, the caregiver device 20 may then be programmed to transmit an arrival signal 510 to the server 40. The caregiver communication device 20, which may include an accelerometer, may then be programmed to detect a change in acceleration data, at which point the caregiver communication device 20 may be programmed to transmit this acceleration data 520 to the hand hygiene beacon 550. The caregiver communication device 20 may then be programmed to receive touch sensor data 540 back from the hand hygiene beacon 550. Once the caregiver communication device 20 receives the touch sensor data 540, it may be programmed to combine this touch sensor data 540 with its accelerometer data 520 into hand hygiene signal 560 which it may transmit to the server 40. The caregiver communication device 20 may then be programmed to return to a passive state. Alternatively, the caregiver communication device 20 may finally receive a hand hygiene notification 530 from the server, which it may then be programmed to indicate to the user that she should return to a hand sanitizing station.

A hand hygiene beacon 550 may include a memory which stores programmed code, and a processor to implement that code. In an embodiment, the hand hygiene beacon 550 may begin in a default passive state until it receives accelerometer data 520. When it receives the accelerometer data 520, the hand hygiene beacon 550 may be programmed to check whether its touch sensor has been triggered by a caregiver communication device 20, either through a physical touch or a nearby interaction. The hand hygiene beacon may then be programmed to send this touch sensor data 540 to the caregiver communication device. The hand hygiene beacon 550 may then return to a passive state.

The server 40 may again remain in a passive state until it receives an arrival signal 510 from a caregiver communication device 20. The server may be programmed to record this arrival signal 510. The server 40 may then be programmed to wait to receive hand hygiene signal 560 from the caregiver communication device 20, at which point the server 40 may then determine whether to send a hand hygiene notification 530 to the caregiver communication device 20. To make this determination, the server 40 may first check whether it has received an arrival signal 510, indicating that the caregiver communication device 20 was in proximity to a hand hygiene beacon 550. The server 40 may then determine whether the hand hygiene signal 560 indicated that the touch sensor was activated. Finally, the server may check whether the accelerometer data contained in the hand hygiene signal indicates that the caregiver spent sufficient time sanitizing her hands. If any of these conditions were not satisfied, the server 40 may be programmed to send a hand hygiene notification 530 to the caregiver communication device 20. If the server 40 determines that each of the conditions were satisfied, the server 40 would return to its default passive state. In alternative embodiments, the checks on the three conditions may be performed in any other order.

In an alternative embodiment, the hand hygiene check may be started when the patient communication device 10 and the caregiver communication device 20 enter into proximity to one another. In this embodiment, the patient or caregiver communication device may send an arrival signal to the server 40, and the server 40 may immediately begin its check on whether the caregiver has sufficiently sanitized her hands. This check may be performed in a substantially similar manner to a check initiated based on proximity to the caregiver communication device 20 to a hand hygiene beacon 550. If the server 40 determines that the caregiver should sanitize their hands, the server 40 may similarly send a hand hygiene notification 530 to the caregiver communication device 20. This may indicate that the caregiver should proceed to a hand hygiene station, at which point the hand hygiene interaction may proceed as in the previous embodiment.

Figure 6:
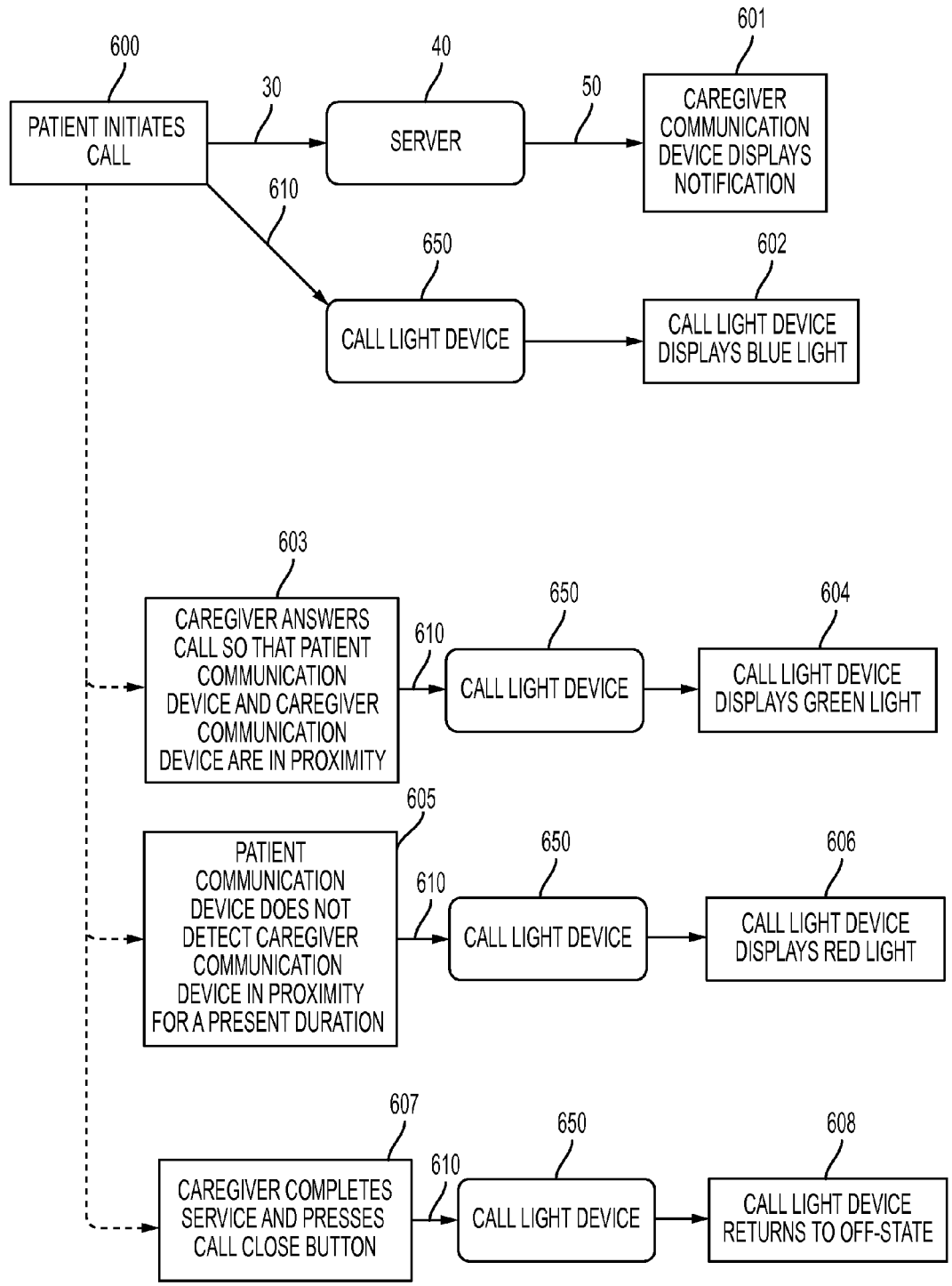
FIG. 6 is a flowchart illustrating an exemplary embodiment of the operation of a call light device.

The present invention may also include a call light device 650, the operation of which is detailed in FIG. 6. Beginning at block 600, a patient will initiate a call as usual from the patient communication device 10. This action will cause the patient communication device 10 to send an assistance signal 30 to the server 40. The server 40 will then send a notification signal 50 to a combination of caregivers, as prescribed by the system administrator, via their caregiver communication devices 20. At block 601, the caregiver's communication device 20 will display this notification, making the caregiver aware of the patient's request. When the patient communication device 10 has sent the assistance signal 30 to the server 40, it will also send a status signal 610 to a call light device 650. This can be done over any wireless communication network of the type described above (e.g., Bluetooth, BLE, NFC, RFID, or IR). Upon receiving the status signal 610, the call light device 650 will display a certain color at block 602. In this embodiment, it would illuminate blue. The call light device 650 may be positioned just outside of the patient's door, so that any staff passing by will have a second indication that that patient has raised a call.

The call light device 650 may have any of at least three other states. The first, indicated at block 603, would be entered once a caregiver has responded to the call and is in proximity to the patient communication device 10. Once this proximity is achieved, either the caregiver's or the patient's communication device 10 will send a status signal 610 to the call light device 650. This will trigger the call light device 650 to illuminate a different color, such as green, at block 604 signaling that the patient's request is satisfactorily being handled. Alternatively, as illustrated at block 605, if a patient's call has gone unanswered in that it does not detect a caregiver communication device 20 within its proximity within a set time, it will send an appropriate status signal 610 to the call light device 650. The duration of this time is again completely configurable by a facility administrator. In this case, the call light will display red at block 606. This provides a visual indication to anyone passing by the light that the patient has a call outstanding, providing a readily visible indication of accountability for the caregivers assigned to that particular patient. Finally, as illustrated at block 607, after a caregiver has provided has provided care to the patient and presses the call close button 24 on the caregiver communication device 20, or if the patient communication device 10 had detected a caregiver in proximity and then having left proximity, the patient or caregiver communication device may send an appropriate status signal 610 to the call light device 650 indicating that service has been completed. In this case, the call light may appear off at block 608.

In an alternative embodiment, any caregiver may provide care to the patient in response to seeing the call light even if that caregiver is not carrying a caregiver communication device 20. This caregiver may actuate a button on the patient communication device 10 to indicate that the caregiver has provided the requested service to the patient. This may be an existing button operated in a different manner, for example by pressing a single button three times in succession. The patient communication device 10 may then send a status signal 610 in the same manner as if it had detected a caregiver closed the call. The call light device 650 would then appear to be in its off-state.

A patient communication device 10 may be in a default passive state until it receives an input for which it is configured to send an assistance signal 30 to the server 40 according to a previous embodiment. The patient communication device 10 may then be programmed to automatically send a status signal 610 to a call light device 650, encoded to indicate that the patient has raised a call. The patient communication device 10 may then operate as in previous embodiments until it detects a caregiver communication device 20 enter its proximity. At this point, the patient communication device 10 may be programmed to send a status signal 610 to a call light device 650, encoded to indicate that a caregiver has responded to the patient's call. If on the other hand the patient communication device 10 does not detect a caregiver communication device 20 enter its proximity for a set time, the patient communication device 10 may be programmed to transmit a status signal 610 to the call light device 650, encoded to indicate that no caregiver has assisted the patient in response to the patient's request. If the patient communication device 10 receives a call close signal from the server 40, the patient communication device 10 may be programmed to transmit a status signal 610 to the call light device 650, encoded to indicate that the patient's call has been satisfied. Alternatively, in place of receiving a call close signal, the patient communication device may be programmed to send a status signal 610 indicating that the patient's call has been satisfied if, for example, a button on the device is pressed three times in succession.

A caregiver communication device 20 may programmed to be in a default passive state until it detects that it is in proximity to a patient communication device 10. The caregiver communication device 20 may then be programmed to send a status signal 610 to a call light device 650, encoded to indicate that a caregiver has responded to the patient's call. Finally, after entering proximity to the patient communication device 10, once the call close button 24 on the caregiver communication device 20 is actuated, the caregiver communication device 20 may be programmed to transmit a status signal 610 to the call light device 650, encoded to indicate that the patient's call has been satisfied.

A call light device 650 may include a memory which stores programmed code, and a processor to implement that code. In an embodiment, the call light device 650 may begin in a default off state until receiving a status signal 610 from a patient communication device 10. The call light device 650 may have code programmed to decode a status signal 610. If the call light device 650 determines that the decoded status signal indicates that the patient communication device 10 has raised a new request, the call light device 650 may be programmed to activate a light of a certain color, for example blue. The call light device 650 may then be programmed to remain in this state until it receives another status signal 610. If the call light device 650 determines that the decoded status signal indicates that the patient communication device 10 detected a caregiver communication device 20 in proximity, the call light device 650 may be programmed to activate a light of a certain color, for example green. The call light device 650 may then be programmed to remain in this state until it receives another status signal 610. If the call light device 650 determines that the decoded status signal indicates that the patient communication device 10 has not detected a caregiver communication device 20 in proximity for longer than a set time, the call light device 650 may be programmed to activate a light of a certain color, for example red. The call light device 650 may then be programmed to remain in this state until it receives another status signal 610. If the call light device 650 determines that the decoded status signal indicates that a caregiver communication device 20 has exited proximity to the patient communication device 10, or that a button on the patient communication device was actuated three times in success to indicate that another caregiver provided service, the call light device 650 may be programmed to deactivate its light, and will remain in this off-state until receiving another status signal.

Figure 7B:
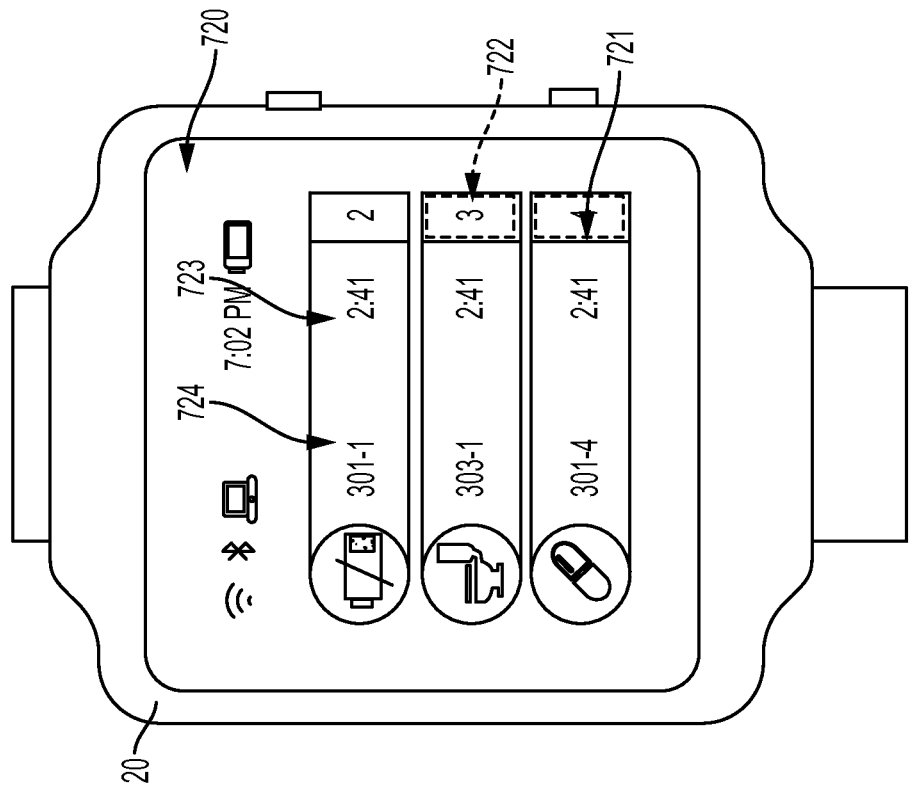
FIG. 7b illustrates a possible embodiment of the display screen of a caregiver wristband device showing various notifications.
Figure 7A:
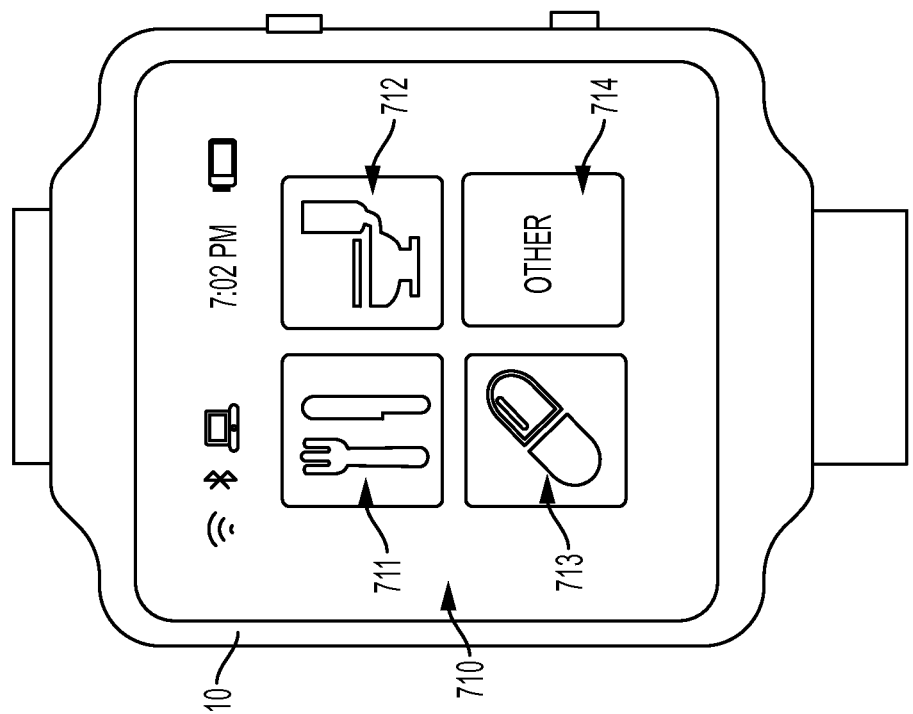
FIG. 7a illustrates a possible embodiment of the display screen of a patient wristband device.

FIG. 7a illustrates exemplary displays on the devices themselves. In this embodiment, the patient communication device 10 has an interface 710 with four exemplary classification buttons 711, 712, 713, and 714. These buttons may be available to the user when he wishes to place a call to a caregiver so that he can indicate to the caregiver the reason for the call. In this embodiment, the classification buttons include a button for requesting food 711, a button for requesting help using the bathroom 712, a button for requesting medication 713, and a button for requesting generic help 714. The classifications may also include requests for services such as cleaning, a blanket, a room temperature problem, a noise problem, or any other patient request. This classification can then be transmitted to server 40, which then transmits that classification to a caregiver communication device 20. In another embodiment, a caregiver may classify an incoming call after attending to the patient using a similar interface.

In FIG. 7b, an embodiment of a caregiver communication device 20 is shown, as it may appear after having received multiple calls, each with a classification. The caregiver communication device 20 includes a user interface 720, which depicts a listing of the notifications which have so far not been taken care of by any caregiver. In this embodiment, notifications 721 are present from two unique patients. It is easily visible that the bottom patient's notification with a logo of medicine is requesting medicine or pain assistance. The other patient's request is also readily discernible to be a bathroom request. Each notification is identified by each patient's device's unique identifier 724, easily allowing the caregiver to identify the patient's location. Also in this embodiment, each notification includes a timer 723, indicating how long the notification has been outstanding. Finally, each notification shows an indication of acuity data 722. Acuity data as used herein refers generally to the degree of need or demand made by patients on the basis of call request frequency or patient encounter frequency. Administration may want to staff caregivers based on acuity results. In this embodiment, the acuity data 722 shows a number for the number of times the patient has requested a call. For example, the patient requesting medication has only raised their request once, whereas the patient who wants bathroom help has sent three separate requests. In alternative embodiments, a light and/or buzzer may be provided which is activated when a notification has been received.

Figure 7E:
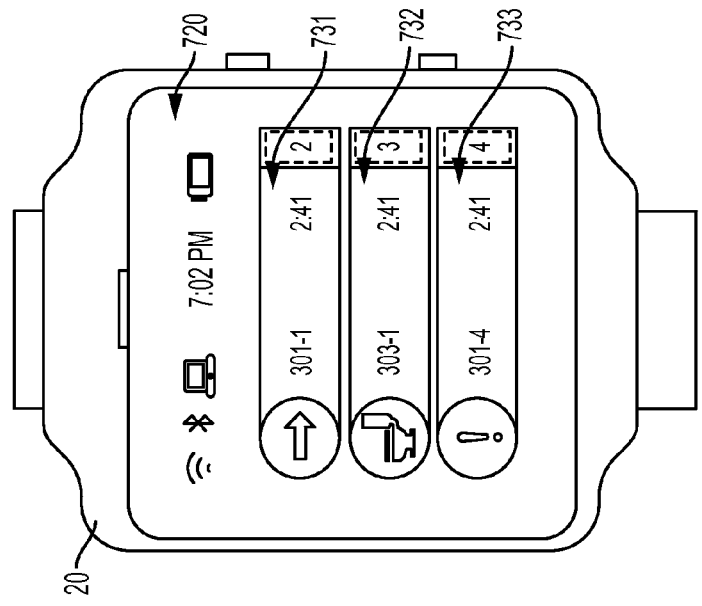
FIG. 7e illustrates a possible embodiment of the display screen of a caregiver wristband device showing notifications being grouped by classification.
Figure 7D:
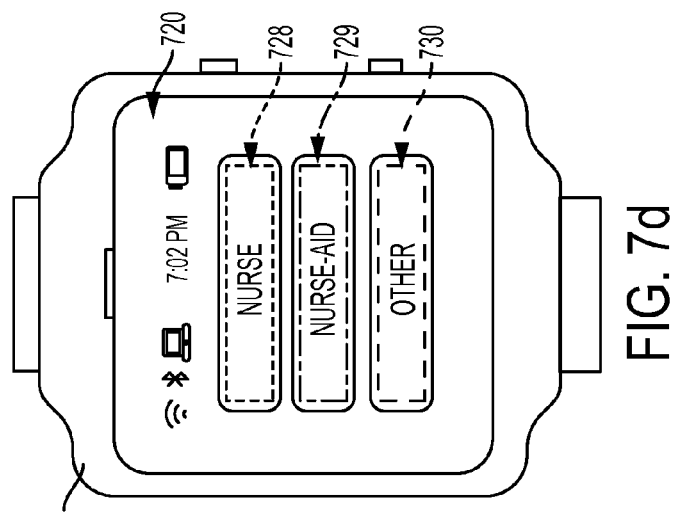
FIG. 7d illustrates a possible embodiment of the display screen of a caregiver wristband device showing a screen after a caregiver has chosen to forward a call.
Figure 7C:
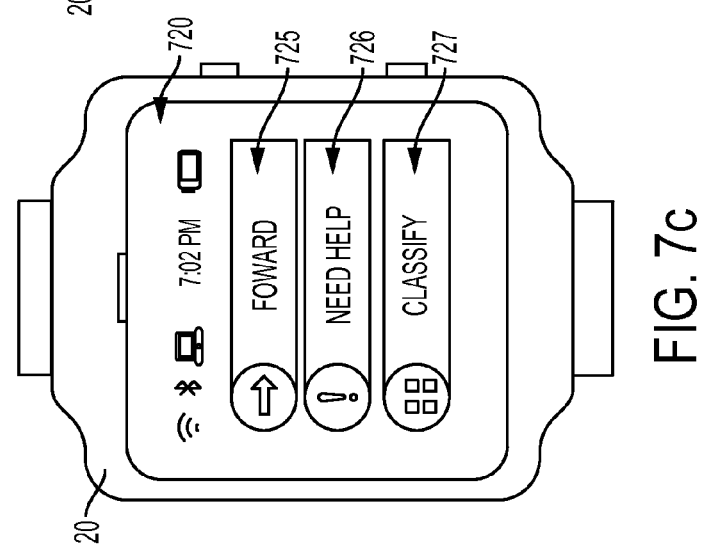
FIG. 7c illustrates a possible embodiment of the display screen of a caregiver wristband device as it may appear when a caregiver has answered a notification and is attending to a patient.

In FIG. 7c, an embodiment of a caregiver communication device 20 is shown, as it may appear when a nurse has answered a notification and is attending to a patient. The caregiver communication device 20 may display on its user interface 720 a forward button 725 for forwarding the call to another caregiver or other person within the facility. The caregiver communication device 20 may display on its user interface 720 a need help button 726 for when the caregiver needs immediate help with the patient. The caregiver communication device 20 may display on its user interface 720 a classification button 727 where the nurse may classify the request in a similar manner to the patient's request classifications.

FIG. 7d illustrates a possible embodiment of the display screen of a caregiver communication device 20 showing a display after a caregiver has chosen to forward a call using the forward button 725. The caregiver communication device 20 may then display on its user interface 720 a button to forward to a nurse 728, a button to forward to a nurse aid 729, or a button to forward to anyone else in the facility 730.

FIG. 7e illustrates a possible embodiment of the display screen of a caregiver communication device 20 showing notifications being grouped by classification. The user interface 720 of the caregiver communication device 20 may also display groups of calls, one each for: standard patient calls, forwarded calls or help requested by other caregivers, emergency help calls, and battery related calls. In this embodiment, there is a forwarded call notification 731, a standard patient call 732 (which is here a request for help using the bathroom,) and a help call 733.

Figure 8:
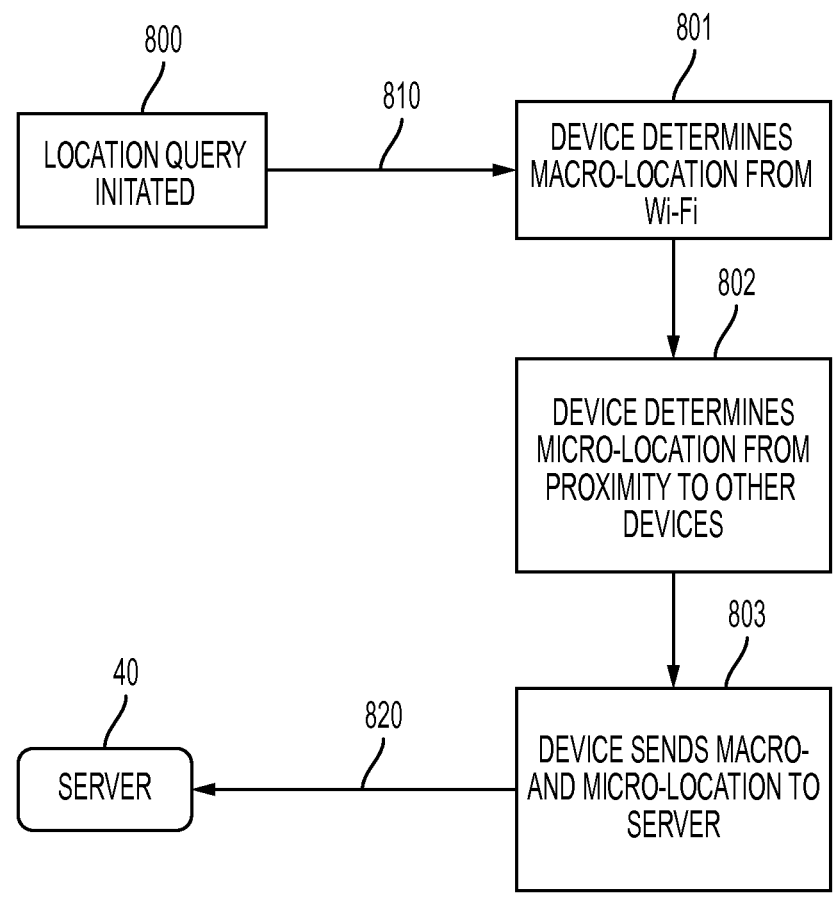
FIG. 8 is a flowchart illustrating an exemplary embodiment of a patient or caregiver device providing its location to a server.

FIG. 8 illustrates the process of determining the location of a patient or caregiver via their communication device. This process may be applied in sharing the caregiver or patient location in response to a notification, or from independent queries initiated by an administrator. The present embodiment begins at block 800, where a query is initiated seeking the location of a caregiver or patient communication device. This query may be initiated automatically by the server 40, by an administrator using the server 40, by a caregiver seeking the location of another caregiver or patient, or by a patient seeking the location of a caregiver. The server 40 will then send a location notification 810 to the caregiver or patient communication device. In block 801, the communication device will then first determine its macro-location from the wireless area network that the systems are operating on. This may, for example, use Wi-Fi. This macro-location may be used to indicate the floor or general wing the patient or caregiver is in. In block 802, the communication device will determine its micro-location by using its proximity functionality to detect nearby communication devices. For example, a caregiver communication device 20 may see that via Bluetooth it is in range of a patient communication device 10 who is in a certain room, or a call light device 650 that is affixed to a certain room. The caregiver communication device 20 will then aggregate the macro- and micro-locations, and send them to the server 40 as shown in block 803. The combined location is sent via a location signal 820 to the server 40, which completes the location query.

A patient or caregiver communication device may be programmed to be in a default passive state until it receives a location notification 810. The patient or caregiver communication device may have code programmed to determine its location. It may then be programmed to determine its macro-location using the wireless area network, for example narrowing its location down to a certain floor and wing of a facility. The patient or caregiver communication device may be programmed to determine its micro-location by detecting the devices currently in proximity, for example a nearby call light device 650, a wander beacon, a hand hygiene beacon 550; or another patient or caregiver communication device. The patient or caregiver communication device may then execute installed code which combines the macro- and micro-locations, and transmits the result to the server 40 in a location signal 820.

The server 40 may again be programmed to remain in a default passive state until it receives a request to query the location of a patient or caregiver communication device. The server 40 may then be programmed to send a location notification 810 to the patient or caregiver communication device. The server 40 may then be programmed to receive a location signal 820 from the communication device. The server 40 may be programmed to decode this location signal and make the location data available to users.

Finally, in other embodiments, caregiver and patient communication devices may be able to send voice communications through the server 40. This will require the patient or caregiver communication device to either be integrated with a speaker and microphone, or have one nearby. This may be in the form of a Bluetooth headset, an independent speaker or microphone positioned near a bed, or in-built speakers and headphones. These voice communications may be possible between any combination of caregivers or nurses, patients, a nursing station, physicians, and administrators. A user may reach another user by inputting their unique identifier into their communication device.

Other features and advantages of the invention will be apparent to those skilled in the art based on the description provided herein. All such features and advantages as well as any modifications within the scope of the appended claims are intended to be part of the invention as herein described.

The invention claimed is:

1. A patient care system, comprising:
a server comprising means for wireless communications;
at least one patient communication device comprising:
a user interface, and
wireless communications means for sending an assistance signal to said server; and
at least one caregiver communication device comprising:
a user interface,
wireless communications means for receiving a notification signal from said server, and
a display indicating said notification signal,
wherein said server includes a server memory storing server instructions and a server processor for executing said server instructions, said server instructions when executed causing said server processor to send said notification signal to a plurality of caregiver communication devices when preset conditions have been satisfied upon receipt of an assistance signal, and further configured to track the receipt of each assistance signal;
wherein said patient communication devices or said caregiver communication devices further comprise a proximity detector;
wherein said wireless communication means of said patient communication devices or of said caregiver communication devices is further configured to send an arrival signal to said server upon arrival of a caregiver in proximity to a patient;
wherein said server is further configured to track each arrival signal;
wherein said user interface of said patient communication device comprises feedback buttons;
wherein said wireless communication means of said patient communication devices is further configured to send a feedback signal to said server;
wherein said server is further configured to track each of said feedback signals; and
wherein said feedback buttons become available once said proximity detector determines that said caregiver communication device is outside of a preset proximity to a patient communication device.

2. The system of claim 1, further comprising:
at least one hand hygiene beacon;
wherein said caregiver communication devices further comprises an accelerometer; wherein said wireless communication means of said caregiver communication device is further configured to send a hand hygiene signal to said server;
wherein said server is further configured to calculate a time duration of hand cleaning from said hand hygiene signal; and
wherein said server is further configured to send a hand hygiene notification to said caregiver communication device if said time duration does not satisfy a time condition or if proximity conditions are not satisfied.

3. A patient care system, comprising:
a server comprising means for wireless communications;
at least one patient communication device comprising:
a user interface, and
wireless communications means for sending an assistance signal to said server; and
at least one caregiver communication device comprising:
a user interface,
wireless communications means for receiving a notification signal from said server, and
a display indicating said notification signal,
wherein said server includes a server memory storing server instructions and a server processor for executing said server instructions, said server instructions when executed causing said server processor to send said notification signal to a plurality of caregiver communication devices when preset conditions have been satisfied upon receipt of an assistance signal, and further configured to track the receipt of each assistance signal; and
further comprising a call light device, wherein said call light device comprises:
wireless communications means for receiving a status signal from said patient communication devices; and
an indicator light, wherein said indicator light changes colors to indicate patient call status, and
wherein said wireless communication means of said patient communication devices is further configured to send a status signal to said call light device.

4. The system of claim 3, wherein:
said one or more patient communication devices further comprise a proximity detector; said wireless communication means of said patient communication device is further configured to send to said server a patient location signal comprising a macro-location and a micro-location based on devices in proximity to said patient communication device;
said plurality of caregiver communication devices further comprise a proximity detector;

said wireless communications means of said caregiver communication device is further configured to send a caregiver location signal comprising a macro-location and a micro-location based on devices in proximity to said caregiver communication device; and said server is further configured to send a patient or caregiver location notification to any of said plurality of caregiver communication devices.

5. The system of claim 3, wherein:

said display of said caregiver communication device displays a list of each open notification received by that caregiver communication device;

said server is further configured to send a completion signal to said caregiver communication device when said preset conditions have been satisfied; and said display of said caregiver communication device no longer indicates said notification signal after receiving a completion signal.

6. The system of claim 3, wherein said preset conditions of said server comprise automatic rounding reminders, said automatic rounding reminders automatically sending said notification signal to said caregiver communication devices at preset intervals.

7. The system of claim 3, further comprising a patient microphone and a patient speaker, wherein:

said wireless communication means of said patient communication device is further configured to send a voice signal to said server;

said caregiver communication device further comprises a microphone and a speaker;

said wireless communication means of said caregiver communication device is further configured to send a voice signal to said server; and said server is further configured to send a voice message to any of said caregiver communication devices and to any of said patient communication devices.

8. A method for providing patient care, comprising:

setting, at a server, preset conditions for sending a notification signal to at least one care giver communication device, and to designated ones of a plurality of caregiver communication devices to which to send said notification signal;

receiving an assistance signal from a patient communication device; tracking said assistance signal;

determining whether to send a notification signal in response to said assistance signal or other preset conditions;

sending said notification signal to said designated ones of said plurality of caregiver communication devices;

updating all of said caregiver communication devices with remaining notification signals after a notification is satisfied; and further comprising receiving a noise level signal from said patient communication device; determining whether said noise level signal satisfies said preset conditions; and sending a noise level notification to said plurality of caregiver communication devices.

9. The method of claim 8, further comprising:

receiving a hand hygiene signal from one of said caregiver communication devices; calculating a time duration from said hand hygiene signal; and determining whether, based on a time condition or proximity conditions, to send a hand hygiene notification to one of said plurality of caregiver communication devices.

10. The method of claim 8, further comprising: requesting location information from said patient communication device or said caregiver communication device;

receiving a patient location signal or a caregiver location signal comprising a macro-location and a micro-location based on devices in proximity to said patient communication device; and sending a location notification, comprising of said macro-location and said micro-location, to any of said caregiver communication devices.

11. The method of claim 8, further comprising:

receiving a voice signal from said patient communication device or said caregiver communication device; and sending a voice message to any of said patient communication devices or said caregiver communication devices.

\* \* \* \* \*